United States Patent
Chen et al.

(10) Patent No.: US 7,770,449 B2
(45) Date of Patent: Aug. 10, 2010

(54) RESISTIVE-TYPE HUMIDITY SENSING STRUCTURE WITH MICROBRIDGE AND METHOD THEREFOR

(75) Inventors: Jung-Tai Chen, Hsinchu (TW); Chia-Yen Lee, Hsinchu (TW); Yii-Tay Chiou, Hsinchu (TW); Chun-Hsun Chu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 305 days.

(21) Appl. No.: 11/808,660

(22) Filed: Jun. 12, 2007

(65) Prior Publication Data

US 2008/0092649 A1    Apr. 24, 2008

(30) Foreign Application Priority Data

Oct. 18, 2006    (TW) .............................. 95138473 A

(51) Int. Cl.
*G01N 27/12*    (2006.01)
(52) U.S. Cl. ................. 73/335.05; 73/29.01; 73/335.11
(58) Field of Classification Search .............. 73/335.05, 73/29.01, 335.11, 335.13, 335.14
See application file for complete search history.

(56) References Cited

U.S. PATENT DOCUMENTS

| | | | |
|---|---|---|---|
| 4,928,513 A | | 5/1990 | Sugihara et al. |
| 5,048,336 A | * | 9/1991 | Sugihara et al. ............ 73/29.01 |
| 5,551,283 A | * | 9/1996 | Manaka et al. ............. 73/29.01 |
| 5,563,341 A | * | 10/1996 | Fenner et al. ............ 73/335.11 |
| 6,840,103 B2 | * | 1/2005 | Lee et al. ................. 73/335.05 |

FOREIGN PATENT DOCUMENTS

| | | |
|---|---|---|
| JP | 63-100352 A | 5/1988 |
| TW | 200508590 | 10/2004 |
| TW | I221900 | 10/2004 |
| TW | M259314 | 3/2005 |

OTHER PUBLICATIONS

K, Rajanna, M. M. Nayak, "Strain Sensors," J. Webster (ed.) Wiley Encyclopedia of Electrical and Electronics Engineering. 1999. pp. 566-580.*
Rittersma, Z. M. "Recent achievements in miniaturised humidity sensors—a review of transduction techniques." Sensors and Actuators A 96 (2002) pp. 196-210.*
Buchold, R., Nakladal, A., Gerlach, G., Neumann, P. "Design studies on piezoresistive humidity sensors." Sensors and Actuators B. 53 (1998) pp. 1-7.*

* cited by examiner

*Primary Examiner*—Lisa M Caputo
*Assistant Examiner*—Punam Roy
(74) *Attorney, Agent, or Firm*—Rabin & Berdo, P.C.

(57) ABSTRACT

A resistive-type humidity sensing structure with microbridge includes a substrate, a sensing portion, and two measuring electrodes. An isolated layer and a bridge are respectively formed on the substrate. The sensing portion includes a resistive and humidity sensing layer. Two measuring electrodes are formed on the resistive sensing layer corresponding to the bridge, so as to fix the sensing portion on the first isolated layer for measuring resistance values of the resistive sensing layer. The material of the humidity sensing layer changes its volume according to humidity, the length of the resistive sensing layer covered by the humidity sensing layer is warped, and the changes of the length of the material for the resistive sensing layer causes variations of the resistance value. Finally, two measuring electrodes are used to measure the humidity value.

8 Claims, 4 Drawing Sheets

RESISTIVE-TYPE HUMIDITY SENSING STRUCTURE WITH MICROBRIDGE AND METHOD THEREFOR

CROSS-REFERENCE TO RELATED APPLICATIONS

This non-provisional application claims priority under 35 U.S.C. §119(a) on Patent Application No(s). 095138473 filed in Taiwan, R.O.C. on Oct. 18, 2006, the entire contents of which are hereby incorporated by reference.

BACKGROUND OF THE INVENTION

1. Field of Invention

The present invention relates to a humidity sensing structure and a method therefor. More particularly, the present invention relates to a structure for sensing the humidity of the environment by using a resistive-type microbridge structure and a fabricating method.

2. Related Art

Recently, the common sensing principles of the humidity sensor include interdigitated electrode (IDE) type, piezoresistive type, surface acoustic wave (SAW) type and optical type etc. The various sensors have their own advantages; however, disadvantages such as low sensitivity, low stability, weak linearity, long responding time and incompensatable excursion value due to the variation of the temperature still exist. In order to solve the bottleneck or the shortcoming of the above technologies and to satisfy the design trend for the sensing module of being miniaturized, portable, and having integrated system, recently the so-called integrated humidity sensing is developed.

In Taiwan patent publication No. 200,508,590 entitled "Micro sensor and Fabricating Method therefor and Sensing Apparatus Using the Same", the capacitance value of a capacitor changes as a cantilever beam bents, so as to change the distance between a fixed electrode layer and a movable electrode layer. Although it is proved that the cantilever beam structure of the microelectromechanical process has the features of higher sensing sensitivity and shorter responding time, because of the process for the top cover element of the fixed electrode in the structure and the subsequent packaging process, the process yield and the packaging cost of the sensing element have the space to be modified. In addition, in the process of the cantilever beam structure of the microelectromechanical process, because only one end is fixed, in the subsequent chip packaging process, the sensing chip of the cantilever beam has an unstable yield. Therefore, the application to the low cost sensor has the room for improvement.

SUMMARY OF THE INVENTION

In view of the shortcomings of the prior art, the problem to be solved by the present invention is to provide a resistive-type humidity sensing structure with microbridge, wherein the resistance value of a suspended microbridge structure with two fixed ends changes because of the variations of the humidity of the environment, and the values of the variations are used to calculate the humidity value of the environment. Another problem to be solved by the present invention is to provide a method of fabricating the resistive-type humidity sensing structure with microbridge.

In order to achieve the above structure, the present invention provides a resistive-type humidity sensing structure with microbridge, which comprises a substrate having a first isolated layer and a second isolated layer, and having an opening opened from the second isolated layer to the first insulated isolation such that the first isolated layer forms a bridge; a sensing portion, consisting of a resistive sensing layer formed by patterning on the bridge and a humidity sensing layer formed on the resistive sensing layer; at least two measuring electrodes formed on two ends of the resistive sensing layer of the sensing portion, so as to fix the sensing portion on the first isolated layer for measuring the resistance values of the resistive sensing layer.

In order to achieve the above method, the present invention provides a method of fabricating the resistive-type humidity sensing structure with microbridge, which comprises providing a substrate; depositing a first isolated layer having a bridge area and a second isolated layer respectively on two surfaces of the substrate; patterning a resistive sensing layer on the bridge area; forming a humidity sensing layer on the resistive sensing layer; forming measuring electrodes on two ends of the bridge area of the first isolated layer, so as to fix the resistive sensing layer on two ends of the bridge area for measuring the resistance values of the resistive sensing layer; and etching the substrate to form an opening from the second isolated layer to the first isolated layer, wherein the opening passes through the opening region except the bridge area of the first isolated layer.

After applying the structure and the fabricating method of the present invention, the extremely high sensitivity, stability, quick responding time, and good process yield are obtained. As compared with the cantilever beam structure of the prior art, the microbridge structure with two fixed ends of the present invention may greatly improve the process yield of the element and reduce the cost of the element. Further, in the present invention, the fabricating of the upper electrode element is omitted, the final packaging flow of the sensing element is simplified, and the high process yield and low element fabricating cost are achieved. In addition, it is compatible with the wafer process, so as to be integrated to a system in package (SIP). In this manner, the volume of the whole sensing element is greatly reduced, and it may be applied to the application requiring the small type packaging element, such as the application of the mobile phone and the pocket size sensor.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus is not limitative of the present invention, and wherein.

DETAILED DESCRIPTION OF THE INVENTION

The preferred implementing method of the present invention is illustrated as follows with the embodiment and with reference to the drawings.

Figure 1:
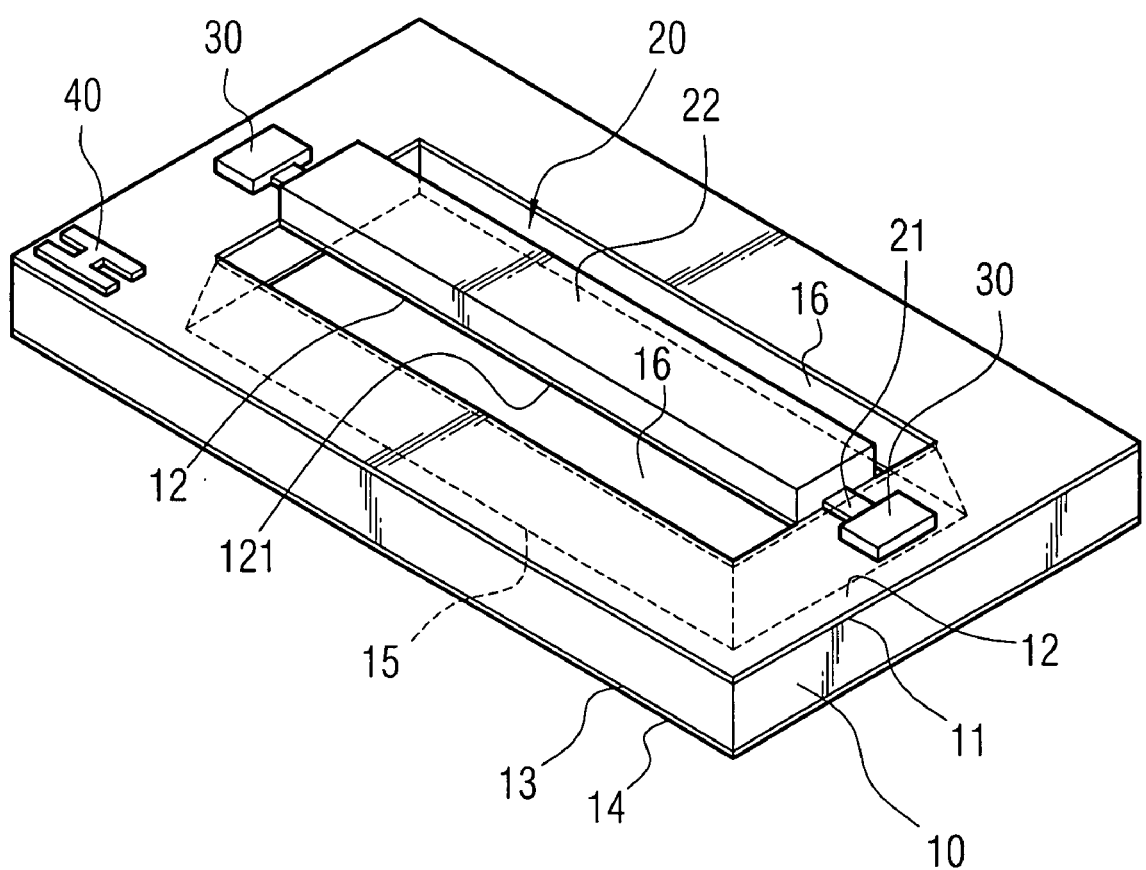
FIG. 1 is a schematic stereogram of a resistive-type humidity sensing structure with microbridge according to one embodiment of the present invention.

Firstly, referring to FIG. 1, a schematic stereogram of the resistive-type humidity sensing structure with a microbridge according to one embodiment of the present invention is shown. The structure includes a substrate 10, a sensing portion 20, and two measuring electrodes 30. The substrate 10 has a first surface 11 and a second surface 13, a first isolated layer 12 being formed on the first surface 11, and a second isolated layer 14 being formed on the second surface 13. The substrate 10 has an opening 15 opened from the second isolated layer 14 to the surface of the first isolated layer 12. After a bridge 121 is reserved on the first isolated layer 12 for the subsequent carrying of the sensing portion 20 (described hereafter), the opening 15 passes through the remaining portion of the first isolated layer 12 corresponding to the opening 15, such that the first isolated layer 12 at two sides of the bridge 121 forms two through-holes 16. The two through-holes 16 may be closed regions. The sensing portion 20 includes a resistive sensing layer 21 and a humidity sensing layer 22, the resistive sensing layer 21 being formed by patterning on the bridge 121, and the material of the resistive sensing layer 21 has the feature of changing the resistance values according to the variations of the length of the material. The humidity sensing layer 22 is disposed on and covering the resistive sensing layer 21, and the material of the humidity sensing layer 22 has the feature that the volume of the material changes according to the variations of the humidity. The measuring electrodes 30 are formed on two ends of the resistive sensing layer 21 of the sensing portion 20, and fix the sensing portion 20 on the first isolated layer 12. The measuring electrodes 30 are formed by a conducting metal or a alloy material, so as to measure the resistance value of the resistive sensing layer 21.

In the above structure, the first isolated layer 12 further includes a temperature compensation sensing electrode 40 formed by the resistive sensing layer material, so as to compensate the resistance values measured under different temperatures, thereby achieving the more exact sensing data.

The material of the substrate 10 of the structure may be the silicon material used to fabricate the semiconductor. The humidity sensing layer 22 may be formed by polyimide. Further, the measuring electrodes may be formed by conductive metal or alloy, such as Au/Cr, Au/Ti, Al/Cr, Al/Ti, Ag/Cr, Ag/Ti, Cu/Cr, or Cu/Ti.

Figure 2:
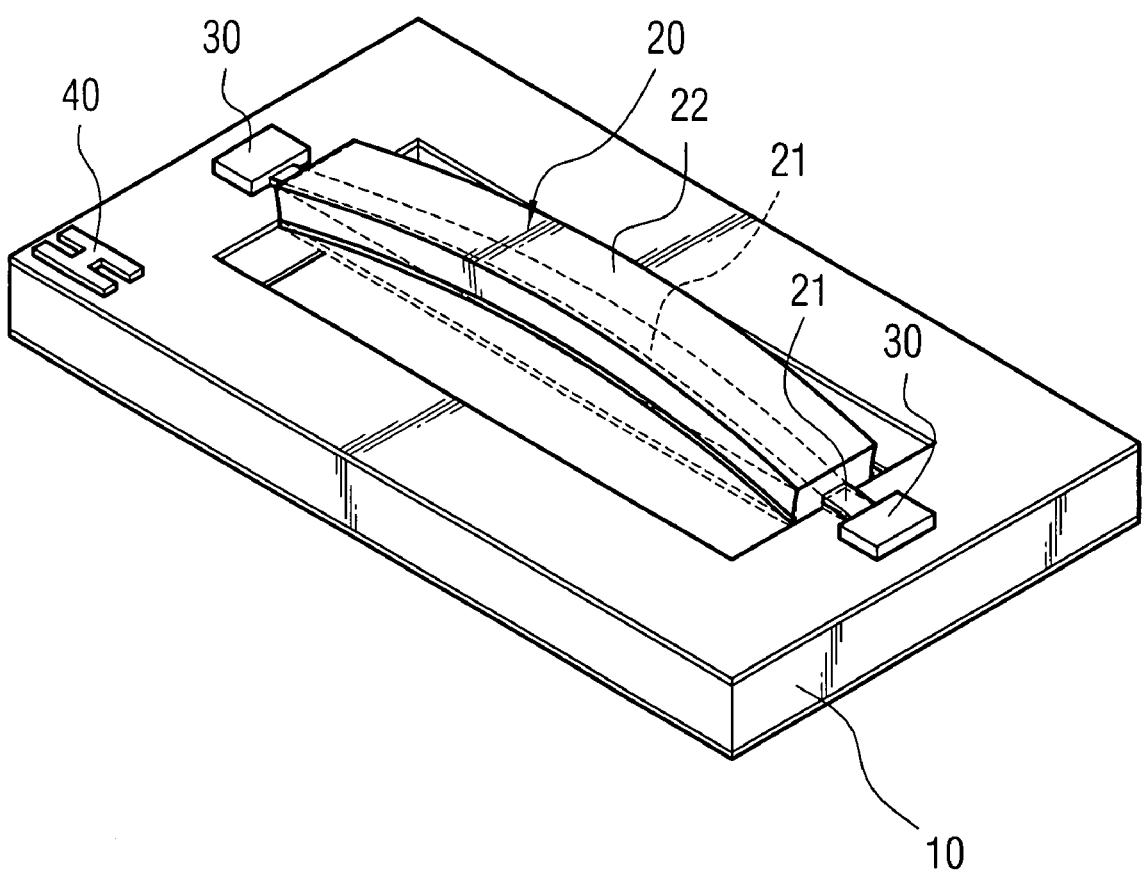
FIG. 2 is a schematic stereogram of the resistive-type humidity sensing structure with microbridge according to one embodiment of the present invention with a deformed sensing portion.
Figure 3A:
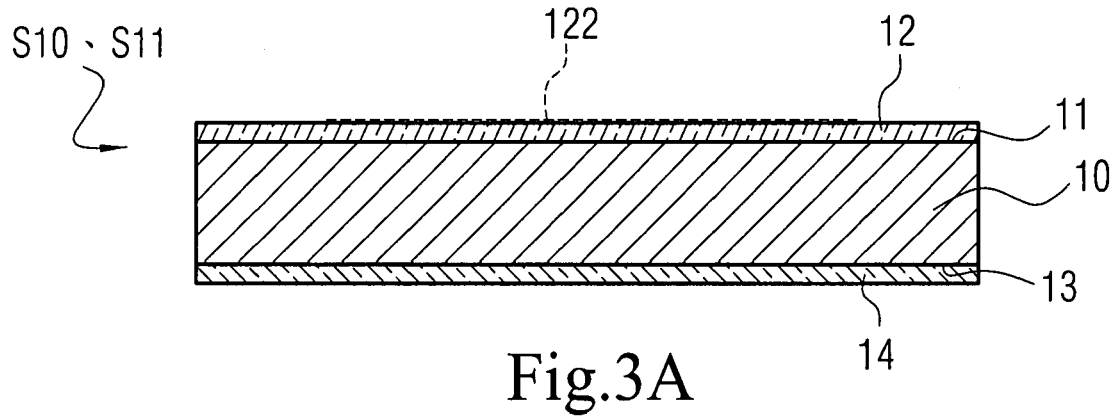
FIGS. 3A to 3E are schematic structural views of the fabricating flow of the resistive-type humidity sensing structure with microbridge according to one embodiment of the present invention.
Figure 3B:
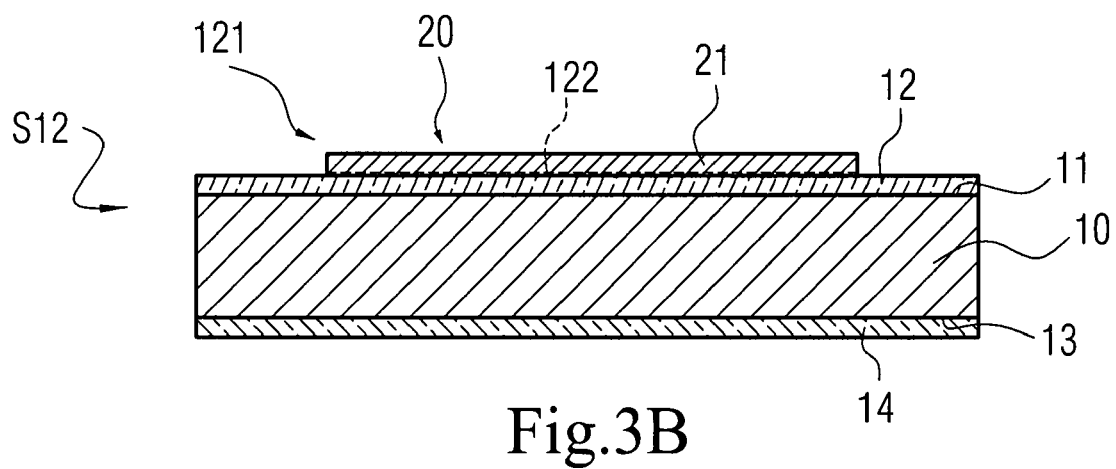
Figure 3C:
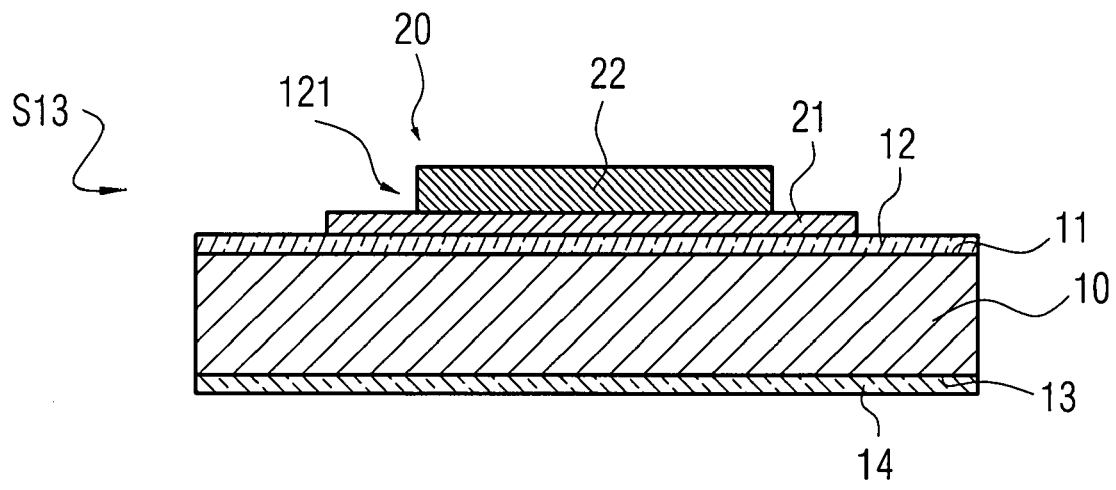
Figure 3D:
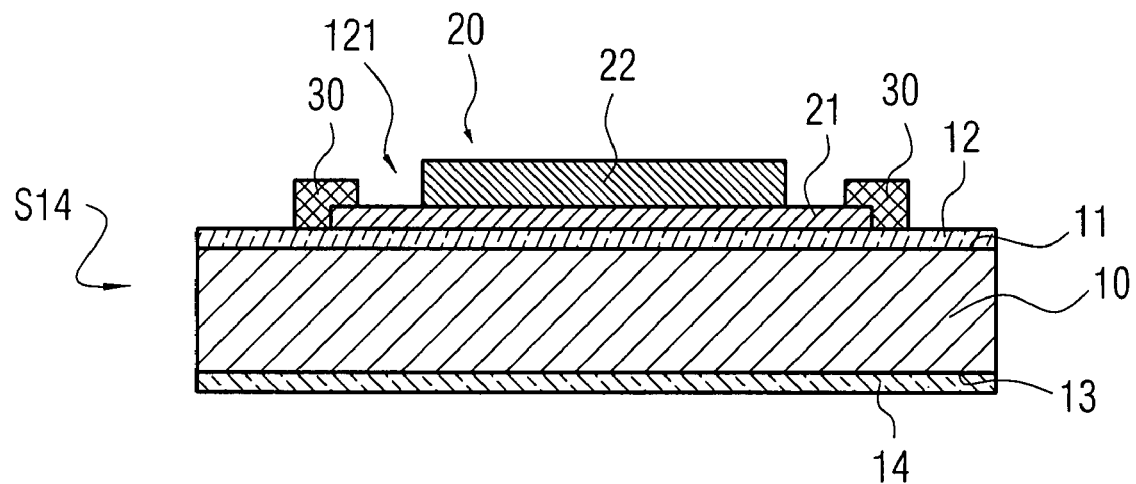
Figure 3E:
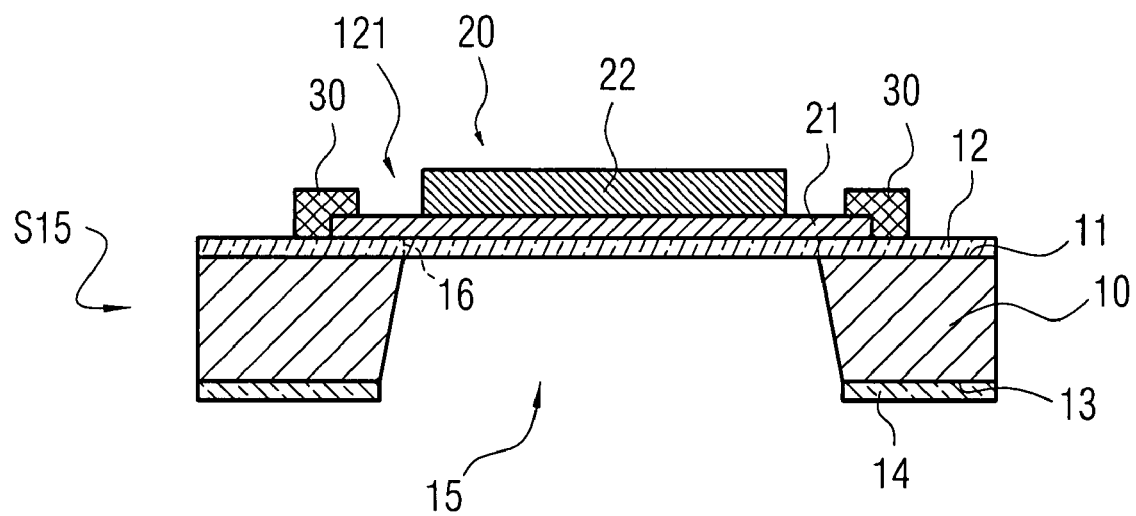

Referring to FIG. 2, a schematic stereo view of the resistive-type humidity sensing structure with microbridge according to one embodiment of the present invention with a deformed sensing portion is shown. The humidity sensing layer 22 in the microbridge structure of the sensing portion 20 absorbs the humidity of the environment and expands, based on the stress, the length of the sensing portion 20 with two fixed ends are buckled and becomes longer. Meanwhile, the resistive sensing layer 21 in the sensing portion 20 structure changes the original length as the microbridge of the whole sensing portion 20 buckles. Therefore, the resistance value of the resistive sensing layer 21 measured by the measuring electrodes 30 naturally changes according to the variations of the length of the resistive sensing layer 21. Finally, the values of the variations of the resistance value of the resistive sensing layer 21 are used to calculate the humidity value of the environment.

Further, referring to FIGS. 3A to 3E, schematic structural views of the fabricating flow of the resistive-type humidity sensing structure with microbridge according to one embodiment of the present invention are shown, and the fabricated stereo structure is as shown in FIG. 1. The fabricating method includes the following steps. A method of fabricating the resistive-type sensing structure with microbridge includes providing a substrate 11 having a first surface 11 and a second surface 13 (S10); depositing a first isolated layer 12 on the first surface 11, and depositing a second isolated layer 14 having a bridge area 122 on the second surface 13 (S11); patterning a resistive sensing layer 21 capable of changing the resistance value according to the variations of the length of the material on the bridge area 122 of the first isolated layer 12, wherein the patterning method may use the standard exposing process (S12); forming a humidity sensing layer 22 capable of changing the material volume according to the variations of the humidity on the resistive sensing layer 21 (S13); forming measuring electrodes 30 on two ends of the bridge 121 of the first isolated layer 12 so as to fix the two ends of the resistive sensing layer 21 for measuring the resistance values of the resistive sensing layer (S14); etching the substrate by dry etching or wet etching to form an opening 15 from the second isolated layer 14 to the first isolated layer 12, wherein the opening 15 passes through the opening 15 region except the bridge 121 of the first isolated layer 12 to form two through-holes 16 (S15).

In the process, the method of forming the humidity sensing layer includes spin coating, stencil printing, vacuum evaporation, coating, screen printing, planographic printing, sputtering, spotting, pouring, or adhering.

Definitely, during step S12, a temperature compensation sensing electrode 40 is further formed on the other region of the first isolated layer 12 except the bridge area 122.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A resistive-type humidity sensing structure with a microbridge, comprising:
   a substrate, having a first surface and a second surface, a first isolated layer being formed on said first surface, and a second isolated layer being formed on said second surface, and having an opening penetrating from said second isolated layer and passing through said first isolated layer to form a through hole after a bridge area is reserved in said first isolated layer;
   a sensing portion, consisted of a resistive sensing layer formed by patterning on said bridge area, and a humidity sensing layer covered on said resistive sensing layer, wherein variations of a length of a material of said resistive sensing layer causes variations in resistance, and a material of said humidity sensing layer changes its volume according to variations of humidity; and
   at least two measuring electrodes, formed on two ends of said resistive sensing layer of said sensing portion so as to fix said sensing portion on said first isolated layer, wherein said two measuring electrodes are formed by conductive metal or alloy material, so as to measure a resistance value of said resistive sensing layer,
   wherein said first isolated layer further comprises a temperature compensation sensing electrode formed on said first isolated layer by the material of said resistive sensing layer.

2. The resistive-type humidity sensing structure with a microbridge as claimed in claim 1, wherein said substrate is of a silicon material layer.

3. The resistive-type humidity sensing structure with a microbridge as claimed in claim 1, wherein said material of said humidity sensing layer is a porous ceramic, organic material or polyimide.

4. The resistive-type humidity sensing structure with a microbridge as claimed in claim 1, wherein said resistive sensing layer is of a platinum (Pt) material.

5. The resistive-type humidity sensing structure with a microbridge as claimed in claim 1, wherein said resistive sensing layer has a pattern of a single straight line, a plurality of parallel straight lines or a plurality of curved broken lines.

6. The resistive-type humidity sensing structure with a microbridge of claim 1, wherein the humidity sensing layer is disposed directly on and covering said resistive sensing layer.

7. A method of fabricating a resistive-type humidity sensing structure with a microbridge, comprising the steps of:

providing a substrate having a first surface and a second surface;

depositing a first isolated layer having a bridge area on said first surface, and depositing a second isolated layer on said second surface;

patterning a resistive sensing layer capable of changing resistance values according to variations of a length of a material on said bridge area of said first isolated layer;

forming a temperature compensation sensing electrode on a region of said first isolated layer other than said bridge area;

forming a humidity sensing layer capable of changing its material volume according to variations of humidity on said resistive sensing layer;

forming measuring electrodes on two ends of said bridge area of said first isolated layer, so as to fix two ends of said resistive sensing layer, for measuring a resistance value of said resistive sensing layer; and etching said substrate to form an opening from said second isolated layer to said first isolated layer, said opening passing through said first isolated layer in a region other than said bridge area of said first isolated layer.

8. The method of fabricating a resistive-type humidity sensing structure with a microbridge as claimed in claim 7, wherein said forming a humidity sensing layer includes forming said humidity sensing layer using at least one of spin coating, stencil printing, vacuum evaporation, coating, screen printing, planographic printing, sputtering, spotting, pouring, and adhering.

* * * * *